United States Patent [19]

Coulthard et al.

[11] 4,292,328

[45] Sep. 29, 1981

[54] THERMOPHILIC AEROBIC DIGESTION PROCESS FOR PRODUCING ANIMAL NUTRIENTS AND OTHER DIGESTED PRODUCTS

[76] Inventors: T. Lionel Coulthard, 4433 W. 6th Ave., Vancouver, B.C., Canada, V6R 1V2; Philip M. Townsley, 4569 W. 13th Ave., Vancouver, B.C., Canada, V6R 2V5; Hugh S. Saben, 819 W. 20th Ave., Vancouver, B.C., Canada, V52 1Y3

[21] Appl. No.: 104,763

[22] Filed: Dec. 18, 1979

Related U.S. Application Data

[63] Continuation-in-part of Ser. No. 935,141, Aug. 21, 1978, abandoned, which is a continuation of Ser. No. 679,994, Apr. 26, 1976, abandoned.

[51] Int. Cl.$^3$ .................... A23K 1/14; A23K 1/12
[52] U.S. Cl. ............................... 426/2; 426/49; 426/52; 426/53; 426/55; 426/56; 426/311; 435/68; 435/804; 435/818
[58] Field of Search ............... 426/53, 2, 49, 52, 56, 426/55, 807, 805.41; 210/15, 2, 6, 7, 11, 14; 435/68, 804, 818; 71/9, 12, 13, 14

[56] References Cited

U.S. PATENT DOCUMENTS

| | | | |
|---|---|---|---|
| 2,917,436 | 12/1959 | Baker | 435/832 X |
| 3,138,447 | 6/1964 | Eweson | 71/12 X |
| 3,462,275 | 8/1969 | Bellamy | 426/53 |
| 3,745,113 | 7/1973 | Fuchs | 210/12 |
| 3,761,237 | 9/1973 | Jeffreys | 71/9 |
| 3,838,198 | 9/1974 | Bellamy et al. | 426/53 |
| 3,864,247 | 2/1975 | Fuchs | 210/12 |
| 3,961,078 | 6/1976 | Stitt | 426/41 |

Primary Examiner—R. B. Penland
Attorney, Agent, or Firm—Christensen, O'Connor, Johnson & Kindness

[57] ABSTRACT

Biochemically degradable organic material, for example, animal waste matter, such as manure produced by hogs, sheep, cattle, chickens and humans is aerobically digested at thermophilic digestion temperatures to produce various digested products, including single cell proteinaceous material suitable for feeding to animals as part of the animals' nutritive diet. Biodegradable material is introduced into a digesting zone that is sufficiently insulated to prevent any substantial heat loss from the digesting material during the digestion process. An oxygenating gas such as air is introduced into the digesting material during all phases of the digestion. The digesting material is simultaneously vigorously agitated. The waste material is placed into the digester at ambient temperatures and is contacted with the oxygenating gas at a rate and is agitated at a level effective to cause thermogenic microbial digestion of the materials present in the waste matter. Since the microbial digestion is thermogenic and because the digester is insulated, the temperature of the digestion waste material will rise from ambient to thermophilic digestion temperatures. Thereafter, the digesting mixture is continuously contacted with the oxygenating gas at a rate and is agitated at a level effective to maintain the thermophilic digestion temperatures for a period of at least four days.

28 Claims, No Drawings

THERMOPHILIC AEROBIC DIGESTION PROCESS FOR PRODUCING ANIMAL NUTRIENTS AND OTHER DIGESTED PRODUCTS

BACKGROUND OF THE INVENTION

This application is a continuation-in-part of prior copending application, Ser. No. 935,141, filed Aug. 21, 1978 abandoned, which in turn is a continuation of prior application Ser. No. 679,994, filed Apr. 26, 1976 abandoned, the benefit of the filing dates of which are hereby claimed under 35 U.S.C. 120.

The present invention relates to aerobic digestion processes that are self generating and self sustaining without the addition of external heat, and in one aspect to a thermophilic aerobic digestion process for producing foodstuffs for animals from animal waste matter. In another aspect, the present invention relates to a thermophilic aerobic digestion process for digesting lignocellulosic materials and other biodegradable materials to produce a product that has a variety of end uses including animal feed, for producing vitamin $B_{12}$, for fixing nitrogen from the air to produce single cell protein for producing amino acids, for producing antibiotics, and for producing enzymes.

In the course of primary agricultural production, animals are utilized in the conversion of basic feed ingredients into milk, meat eggs and related high nutrient sources for human consumption. In the conversion process, animals eat foodstuffs such as grass and grain and create byproducts, namely manure, which is presently classed as a waste product and pollutant. The growing human population density in North America and throughout the world has required a more intensive and selective animal production to meet the increasing demand for foodstuffs for human consumption. The result of the higher demand for food production is a greater animal population with a concomitant and consequential pollution potential caused by an increasing amount of animal waste products created. Moreover, the more intensive animal production facilities are growing in competition with expanding urban development, compounding the pollution problem, whereas in the paste agricultural areas contained small, widely spread farms that did not create a burden on the environment through their waste products.

Presently, as in the past, animal waste products are disposed of by any convenient method. For example, the animal waste products have been spread in untreated form over the land as a fertilizer. As the volume of animal waste products has increased, the latter disposal method has become inadequate as the untreated waste product tends to contaminate the surrounding streams and rivers as well as adversely affect the subterranean water. Moreover, it has become increasingly common for the runoff from animal feedlots to gain access to the streams and rivers in large quantities, causing a serious pollution problem. Consequently, interest has been recently spurred toward finding a means to detoxify animal waste products and to render them harmless to the environment. Even more recently, interest has been developed in creating a foodstuff from the animal waste products that can be refed to animals as at least a portion of their nutritive diet.

Several techniques to detoxify animal waste products have been attempted, including forced drying and microbiological digestion. Drying of the byproducts is a relatively expensive process requiring a significant capital investment in equipment and controls as well as requiring a high external energy input. Thus, more interest has recently been generated in microbiological digestion processes as there is a potential that a smaller capital investment and lesser amounts of external energy input will be required.

One attempt at microbiologically digesting animal waste products is disclosed in U.S. Pat. No. 3,462,275 issued to W. D. Bellamy for a waste conversion process and product. Bellamy inoculates animal waste matter with thermophilically active microorganisms from sources such as compost piles and from hot springs and anomalous hot earth areas. Bellamy flocculates animal waste matter by the addition of flocculating agents to reduce the concentration of inorganic solids and thereafter inoculates the supernatent liquor with a thermophilic aerobic microorganism. Thereafter, the inoculated waste product is placed in a thermophilic aerobic growth chamber and heated to thermophilic digestion temperatures. After digesting for a short period of time, the digested product is separated into a solid and liquid by centrifuging and filtering. The liquid is disposed of by conventional means while the solid portion is dried and packaged for use as an animal foodstuff. Although the Bellamy process is, on its face, efficacious to produce an animal foodstuff from animal waste matter, it is to be observed that the Bellamy process requires the application of external heat and uses only a very small portion of the input product.

Accordingly broad objects of the present invention are to provide a process for biodegradable organic material such as animal waste products, sewage sludges, organic domestic and industrial wastes, and animal, vegetable and fruit processing plant wastes, under thermophilic and aerobic conditions to produce a proteinaceous foodstuff therefrom that can be refed to animals as part of the animals nutritive diet. Additional objects of the present invention are to provide a thermophilic, aerobic digestion process that requires the addition of no external heat to initiate and raise the digestion temperature to the thermophilic range; to provide a thermophilic digestion process that deodorizes and pasteurizes animal waste products and renders them harmless to the environment; to provide a thermophilic aerobic digestion process that increases the protein content of the digestion product over the protein content of the initial organic material being digested; to provide a thermophilic aerobic digestion process that kills all pathogens in organic material such as waste products, including coliform and salmonella bacteria, virus, worms and larvae; to provide a process for stabilizing sewage sludges and other biodegradable material so that they can be disposed of economically and safely and to provide an economical thermophilic aerobic digestion process that requires a minimum capital investment and which therefore can be installed on site at animal production sites.

It is a further broad object of another aspect of the invention to provide a thermophilic aerobic digestion process that is capable of digesting lignocellulosic material. Other objects of this aspect of the invention are to provide a thermophilic aerobic digestion process that can microbiologically attack the lignin in the lignocellulosic material and thus free the cellulose cells for digestion in a very short time; to provide a process for producing enzymes that will break down the cellulose thus made available; to provide a thermophilically digested product from lignocellulosic materials that does not contain undesirable byproducts such as those yielded in chemical pulping processes and that does not produce the undesirable odor and disposal problems normally associated with pulping processes; to provide a thermophilic aerobic digestion process for lignocellulosic materials that yields a new source of nutrients in digestible form for feeding to animals; and to provide a process that fixes nitrogen from the air to produce a digestion product containing more usable protein than the original lignocellulosic starting material.

Still further objects of the present invention are to provide methods for producing vitamin $B_{12}$, methods for producing amino acids such as lysine and methionine, and methods for producing enzymes such as cellulase.

SUMMARY OF THE INVENTION

In accordance with the foregoing objects, and other objects that will become apparent to one of ordinary skill in the art after reading the following specification, the present invention in its broadest aspects provides a process for using thermophilic bacterial microorganisms for digesting an aqueous mixture of biochemically degradable organic material under aerobic and thermophilic conditions. The mixture is introduced into a digester that is sufficiently insulated to prevent substantial heat loss therefrom. An oxygenating gas is continuously introduced into the mixture. Additionally, the mixture is continuously, mechanically, and vigorously agitated while the oxygenating gas is being introduced. The oxygenating gas is introduced at a rate and the mixture is agitated at a level effective to cause and promote the temperature of the mixture to rise from ambient temperatures, through mesophilic temperatures, to a temperature of at least 55° C. without the addition of external heat to the mixture. The oxygenating gas is introduced and the mixture is agitated until the material is digested to the desired degree. The oxygenating gas is initially supplied at a rate sufficient to maintain a dissolved oxygen level in the mixture effective to supply the biological oxygen demand of the mixture. Once the temperature of the mixture reaches 55° C., the mixture is agitated at a level and the oxygenating gas is introduced at a rate effective to maintain the temperature of the mixture at at least 55° C. without the addition of external heat. It is preferred that the oxygenating gas be introduced at a rate sufficient to raise the dissolved oxygen level in the mixture to and maintain it above 1.0 mg/l. The biodegradable organic material digested in accordance with the present invention can be any of a variety of materials including fecal matter such as animal waste and sewage sludge, and plant wastes such as normally discarded by a potato processing plant. The digestion product generally comprises a single cell proteinaceous material that can be fed to animals as at least a portion of their nutritive diet. Additionally, it has been found that vitamin $B_{12}$ is produced by the thermophilic digestion process of the present invention and can be extracted from the digestion product.

In another related aspect of the present invention, organic material that is normally not digestible via aerobic digestion processes, such as lignocellulosic material can also be digested at a practical rate. The agitation and aeration is effected as with fecal matter and other biodegradable material in accordance with the invention to raise the temperature of the digesting mass to about 55° C. and to maintain the temperature of the mass at at least 55° C. Surprisingly, the lignin in the lignocellulose material is broken down to first form a digestion product comprising cellulose cells. If the thermophilic digestion process is continued, the cellulose is also converted to single cell protein. Moreover, nitrogen from the air is fixed in the single cell protein thus producing a digestion product containing a greater amount of protein than the original lignocellulose material. This single cell protein can again be fed to animals as a portion of their nutritive diet. In addition, enzymes can be extracted from the digestion product, which enzymes are useful in breaking down the cellulose structure in wood.

In yet another aspect of the present invention, the organic biodegradable material can be seeded with an organism that is capable of producing amino acids such as lysine and methionine. These organisms, when digested in accordance with the present invention at thermophilic temperatures, will produce additional amino acids, which have obvious utility.

DETAILED DESCRIPTION

Microbiological digestion processes are those in which microbes, such as bacteria, digest biodegradable organic material and produce certain kinds of byproducts, depending upon the digestion environment. Typical aerobic digestion processes of the prior art occur under conditions where oxygen is available to at least a portion of the microbes in the digestion mixture. The bacteria operating in a particular aerobic digestion process are classified as psychrophilic, mesophilic and thermophilic, dependent upon the temperatures at which the particular organisms survive and metabolize. Those of particular interest to the present invention are the thermophilic bacteria which generally digest organic matter at temperatures from 49° C. up to 80° C. and sometimes higher.

In one embodiment of the present invention, thermophilic bacteria that can digest animal waste matter under aerobic conditions are employed to produce a proteinaceous digested product that can be refed to animals. Basically, animal waste matter is introduced into a digesting zone, hereafter referred to as a digester. The digester is sufficiently insulated to prevent any substantial amount of heat loss through the walls and the bottom of the digester. The top of the digester can be left open to the atmosphere, but is essentially insulated by an aerated, foam-like layer of material as will be hereinafter described. After the waste material has been introduced into the digester, an oxygenating gas, such as air, is introduced into the digester at a predetermined rate to create an aerobic environment for the bacteria naturally occurring in the animal waste matter. At the same time the animal waste matter in the digester is vigorously agitated so that all of the bacteria in the digester have oxygen readily available for purposes of metabolizing and digesting the organic matter present in the digester. As will hereinafter be explained, the rate at which the oxygenating gas is introduced into the digester and the level of agitation of the waste material in the digester is critical. That is, a substantial amount of air must be continuously introduced into the digester while the waste material is continuously and vigorously agitated in order to achieve the results of the present invention. The oxygenating gas is introduced into the digester at a rate and the waste material is vigorously agitated at a level effective to cause the naturally occurring microorganisms in the digester to begin digesting the organic material under aerobic conditions. Normally, the waste matter when placed in the digester is at ambient temperatures, which are somewhat below the thermophilic digestion temperature range. However, by agitating the waste materials sufficiently and by introducing an effective amount of oxygenating gas, the microorganisms begin to digest the waste materials with a thermogenic biochemical reaction. Since the digester is sufficiently insulated to prevent any substantial heat loss from the digesting materials, the heat generated by the biochemical reaction will be substantially retained within the digesting mass, causing the temperature of the digesting material to rise and ultimately achieve the thermophilic digestion temperatures. It has been found that under the conditions described below, the animal waste matter will reach thermophilic digestion temperatures in from two to four days after the waste matter is introduced into the digester under batch reaction conditions from an ambient temperature of from 0° to 20° C.

After the waste matter has reached thermophilic digestion temperatures in the digester, the oxygenating gas is continuously introduced at a rate and the waste matter is still vigorously agitated at a level effective to maintain the temperature of the waste matter in the thermophilic digestion temperature range. Again, the rate at which the oxygenating gas is introduced into the digester and the level at which the waste matter is agitated is critical. If the rate at which the oxygenating gas is introduced into the digester drops below a certain critical rate, the thermophilic microorganisms digesting the waste material will cease to be sufficiently active to maintain the temperature within the thermophilic digestion temperature ranges. However, if the rate of introduction of oxygenating gas is too high, the digesting mixture will tend to cool and drop below the thermophilic temperatures required by the present invention. It is believed that this cooling effect is brought about either or both by heat transfer from the digesting mixture to the gas being introduced and the subsequent escape of the thus heated gas to the atmosphere or by an excess amount of oxygen being present, which may be toxic to certain thermophilic organisms. Likewise, if the agitation level drops below a certain level, namely below a level at which all parts of the digesting mass are in turbulent movement so that no part of the digesting mass is undergoing an aerobic digestion, the same adverse results will occur, i.e., the thermophilic microorganisms will not be able to maintain the temperature of the digesting waste material in the thermophilic range.

The thermophilically digesting waste matter is continuously agitated and aerated to maintain the thermophilic digestion temperatures for a period of at least four days. After this minimum digestion period, the protein level of the resulting digested product has been increased on the order of from 2% up to 25% by weight over that of the original waste material. It has been found that waste material digested in accordance with the foregoing process can be successfully fed to ruminant animals at levels up to about 50% by weight of their normal nutritive diet, to swine at levels up to about 30% by weight of their normal nutritive diet, and to poultry at levels of up to about 15% by weight of their normal nutritive intake, depending upon whether the digested product is fed in a liquid form directly from the digester of whether it is first dried.

The foregoing process produces a proteinaceous material that can be refed to animals from what, in general, is referred to herein as "animal waste matter." By "animal waste matter" it is meant the fecal matter of manure produced as a byproduct of an animal's digestion of food. There is no limitation as to the particular type of digestive system of the animal as the process has been successfully operated utilizing cattle manure, hog manure, sheep manure, horse manure, mink manure, chicken manure, or human waste as the starting material. It is to be understood that the microorganisms naturally occurring in the animal waste matter are those which are responsible for the microbial action in the digestion process of the present invention. No inoculation from a cultured bacteria medium is necessary to effect the initial temperature rises in the process of the present invention or to maintain the thermophilic digestion temperatures once they are reached. Preferably, the animal waste matter is in raw form and has not been subjected to any pretreatment processes. It is also preferable that the animal waste matter be reasonably fresh, although it is possible to effect the present invention with animal waste matter that has been in storage for up to thirty days or longer or which has received an aerobic treatment, such as activated human sludge.

To be economical, it is normally preferred that the dry solids content of the fecal matter in the digester be at least about 5% by weight based on the total material in the digester. It has been found that if the dry solids content of the waste matter in the digester is initially below about 5% by weight that the digestion process of the present invention cannot be effected. That is, with any level or aeration and agitation it is difficult, if not impossible, to promote the desired temperature rise from ambient conditions to thermophilic digestion temperatures by the action of the naturally occurring thermogenic bacteria. Moreover, even if it is possible to reach thermophilic digestion temperatures with solids content less than 5% by weight during the intial phases of the process, the thermophilic digestion temperatures cannot be maintained for an adequate amount of time to digest the waste materials. It is believed that this level of solids content is necessary to provide a sufficient amount of digestible material for the thermophilic, thermogenic bacteria to continuously thrive and to yield a sufficient amount of heat to cause the desired temperature rise and temperature maintenance in the digesting material.

Since manure from different animals will vary in its original water content when excreted, it may be necessary to add water to the animal waste matter prior to being placed in the digester or immediately after it is placed in the digester. The addition of water will bring the viscosity of the waste matter down to a reasonable level so that large amounts of energy are not required to agitate the waste matter. Under conditions in many animal feed lots, the fecal material from the feeding pens is washed out with a water spray into troughs and stored in tanks for a short period of time. The aqueous fecal matter so stored is normally adequate for direct placement into the digester. If the dry solids content of the animal waste (fecal) material placed in the digester is much greater than about 20% by weight, the power requirements for agitating the digesting material rise significantly because the viscosity of the material is relatively high; thus it is preferred to maintain the dry solids content of the fecal material below about 20%. It has been found that the most efficient and economical processing conditions from the agitation energy input standpoint dictate a dry solids content of between about 5% by weight and about 10% by weight of the total aqueous mixture in the digester when the process is initiated.

It is absolutely necessary in order to effect the process of the present invention that the digester be insulated to prevent substantial heat loss through the walls and the floor or bottom of the digester. Normally, digesters are constructed from steel but can be constructed from fibreglass reinforced polyester resins. Normally a layer of closed cell foam insulation such as a polyurethane foam having a thickness of on the order of 1 to 3 inches is adequate to insulate the sides and the bottom of the digester to prevent substantial heat loss. If ambient conditions would normally cause a higher heat loss, such as high wind velocities or very low temperatures (below 0° C.), additional insulation may be required to adequately prevent heat loss so that the process temperatures can be initially raised to the thermophilic range and thereafter maintained in the thermophilic range for extended periods. The digester size is not critical, but as will be seen later, the amount of agitation and rate of aeration must be adjusted in accordance with the volume of digesting material present in the digester.

A layer of foam is formed on the surface of the digesting material by the aeration process, which layer serves to insulate the top of the digester to prevent heat loss in an upward direction. As will be seen later, the preferred form of aeration causes the air to be dispersed into relatively small bubbles in the digesting material. This aeration procedure desirably produces a foam layer comprising relatively small bubbles on the top of the liquid digesting material, which provides an excellent insulating layer to prevent substantial heat loss in an upward direction. It is preferred that the thickness of the foam layer be maintained at about 6 to 8 inches or less. If it is not, the foam layer will tend to grow beyond that height and possibly spill over the open top of the digester. The foam level is maintained at 6 to 8 inches or less by using a conventional foam breaker mounted on a platform positioned across the top of the tank.

The pH of the starting materials need not be adjusted as the slightly alkaline pH of relatively fresh fecal matter is adequate to support the desired microbiological reaction. It is preferred however that the pH of the material be maintained between about 5.0 and about 8.5 with a most preferred pH of on the order of from 5.9 to 7.5.

The thermophilic digestion temperatures that are considered to be operable within the purview of the present invention are in the range of from 49° C. to about 80° C. although the best results in accordance with the present invention have been obtained when the thermophilic digestion temperatures have been maintained above 55° C., and most preferably in the range of from 55° C. to 75° C. If the digested product is to be refed or safely disposed of, it is most important that the thermophilic digestion temperatures be maintained above about 55° C. for a minimum period of about ten minutes to thirty minutes in order that certain pathogens, such as salmonella bacteria, coliform bacteria and helminths are destroyed. Certain viruses and other pathogens present in the mixture may require a somewhat longer residence time for a complete kill at 55° C. If the temperatures are not maintained for a sufficient period of time, certain of the pathogens may carry over into the digested product and thus contaminate it so that is cannot be safely refed to animals. If, however, the thermophilic digestion mixture is maintained at a temperature of above 65° C. for on the order of about 10 minutes or more, it has been found that the pathogens, viruses and worm larvae will be killed.

The rate at which the digesting material is aerated is critical. If insufficient oxygenating gas, preferably air, is supplied to the digesting tank, the thermophilic digestion temperatures cannot be achieved or maintained, and thus the digested product containing proteinaceous material capable of being refed to animals will not be produced.

During the initial start up phase of the digestion process during which the temperature of the animal fecal material is being raised to thermophilic digestion temperatures, the digesting material exhibits a very high biological oxygen demand (BOD). During this initial period it is critical that the BOD requirements of the digesting material be met by supplying a sufficient amount of oxygenating gas. If the BOD requirements are not met, the proper succession of microorganisms will not develop and thus the temperature of the digesting mixture will not rise to the thermophilic range. Dissolved oxygen concentrations on the order of 0.2 mg/l. have been observed during initiation of the process while oxygenating air is being supplied to the mixture to raise the temperature of the digesting mixture from ambient to thermophilic temperatures. This low level of dissolved oxygen may remain for two to four days. However, when the temperature of the digesting mixture approaches and achieves the thermophilic digestion temperature range, the dissolved oxygen level will begin to rise.

Once thermophilic digestion temperatures are achieved, the dissolved oxygen level of the digesting mixture will rise to about 1.0 mg/l. or higher when the initial aeration rate is held constant. If the initial aeration rate is continued as the dissolved oxygen level increases, the foam produced on top of the digesting mass will significantly increase. Thus it has been found necessary in most cases to reduce the aeration rate once thermophilic digestion temperatures have been achieved to decrease the foam production to a level that can be managed by a conventional foam breaker. While decreasing the foam production, however, the dissolved oxygen level in the digesting mass must be maintained above about 1.0 mg/l. when the fecal matter is digesting at thermophilic digesting temperatures. It is preferred that the oxygen level be maintained between about 1 mg/l. and 4.5 mg/l., although dissolved oxygen levels up to the oxygen saturation point of the fecal matter are effective. The preferred temperature range of from 55° C. to 75° C. is obtained when the dissolved oxygen level is maintained between about 2.0 mg/l. and about 3.0 mg/l. If the dissolved oxygen level drops below the 1.0 mg/l. level while the thermophilic digestion temperatures are being maintained, the rate of protein production will be lowered as well as the nutritive quality of the digested end product. Moreover, the proper succession of microorganisms necessary to achieve the thermophilic digestion may not be developed if the dissolved oxygen level is allowed to drop below 1.0 mg/l. Also, as stated above, the rate at which oxygenating air is introduced cannot be too high or the temperatue of the digesting mixture will drop below the thermophilic temperature range required by the present invention.

The preferred oxygenating gas is air, primarily because of its ready availability and the generally low cost of compressing atmospheric air sufficiently to inject it into the digester. When air is introduced as the oxygenating gas into the bottom of a digester having a diameter of four feet and a liquid depth of about four feet, it has been found that a rate of aeration of at least about 0.02 volumes of air per minute per unit volume of digesting material, that is the total aqueous mixture, is normally required to initially raise the waste matter to thermophilic digestion temperatures. If the rate of air introduction exceeds about 0.02 volumes of air per minute per volume of digesting material in this size digester, foam production will be excessive and may cause foam to overflow from the digester. On the other hand, aeration rates below 0.01 volumes of air per minute per volume of digesting material will produce an insufficient amount of foam to insulate the top of the digester and to supply the microorganisms with sufficient oxygen to create the thermogenic digestion required to raise the temperature of the digesting mass to the thermophilic temperature range. After the thermophilic digestion temperatures have been reached in a digester of the size just mentioned, the best digested product has been obtained when air is introduced at rates of between 0.01 and 0.02 volumes of air per minute per volume of digesting material.

The exact quantity of oxygenating gas that must be introduced into the digesting mass in accordance with the present invention is critical in that if too much or too little is introduced, either the requisite temperature rise to thermophilic digesting temperatures will not be achieved, or the temperatures cannot be maintained in the thermophilic digesting range. The exact amount of oxygenating gas that must be introduced varies with the quantity of the digesting mass, the solids content of the mass, the temperature at which the mass is digesting and the efficiency with which oxygen is transferred from the oxygen gas to a dissolved state in the digesting mass. In any event, the critical parameter is that a sufficient amount of oxygenating gas be introduced during the initial digestion phase so that the thermogenic microbiological activity in the digesting material will cause the temperature of the material to rise from ambient to the thermophilic range. Thereafter, it is critical that an amount of air be supplied that is effective to maintain the thermophilic digestion temperatures for a period of at least four days.

Another descriptive parameter for the critical aeration rate of the digesting material is that each of the microbes in the digesting waste matter must be exposed to available oxygen at least once every two and one-half minutes. This exposure rate is accomplished not only by aerating at the rates set forth above but also by vigorously agitating the digesting waste matter at a level adequate to maintain this exposure rate. During both the initial start-up phase of the digestion reaction and while the thermophilic digestion temperatures are being maintained, the waste material must be sufficiently agitated so that every portion of the digesting material is moving within the digester. Moreover, the agitation must be at a sufficient level to cause every portion of the surface of the digesting material to roll, indicating that the digesting material is in a very turbulent condition within the digester.

The foregoing contact rate between the microbes in the digesting material and the dissolved oxygen in the digester was empirically determined by observing the rate at which the bacteria consume the available oxygen. That is, if aeration at the rates set forth above is stopped, the bacteria will completely utilize the available oxygen supply, i.e., the dissolved oxygen, in the digesting material in about two and one-half minutes or less. For example, an aqueous mixture of fecal matter containing about 10% by weight of dry solids that is saturated with oxygen and that is digesting at 60° C. in accordance with the present invention will consume all of the available oxygen in the mixture in about two and one-half minutes when the supply of oxygenating gas to the mixture is stopped but the agitation is continued. Thus the aerobic bacteria present in the material being digested in accordance with the present invention oxidizes organic matter at a very rapid rate, requiring rapid recontacting with available oxygen at least every two and one-half minutes.

Moreover, it has been found that it is necessary to continuously cleanse the digesting material of carbon dioxide. Removal of the carbon dioxide will allow a better contact rate between the microorganisms in the digesting material and the dissolved oxygen available in the digesting mixture. Carbon dioxide is removed from the digesting material in accordance with the present invention by the oxygenating gas passing through the mass of digesting material, which replaces the carbon dioxide and drives the carbon dioxide to the surface of the digesting material. The carbon dioxide can then escape from the digester through the foam layer normally formed on the top of the digesting material.

In a most preferred form of aeration and agitation, the oxygenating air is introduced into a cylindrical digesting mass via a sparger pipe adjacent the bottom of the cylindrical mass. The sparger pipe contains a check valve to prevent digesting material from entering the pipe. Air is supplied to the pipe by an air compressor at the rates described above. A turbine blade mounted at the bottom of a rotatable shaft oriented coaxially with the cylindrical mass is positioned immediately above the outlet of the pipe. The turbine blade is so oriented and configured as to drive fluid upwardly from adjacent the bottom of the digesting mass and force it up through the central portion of the digesting mass, causing the liquid to roll on the surface of the digesting mass. Thereafter, the liquid circulates down the sides of the digesting mass and is recirculated by the turbine. As this occurs, the air introduced from the pipe is fed directly through the turbine blade so that the shearing action of the turbine blades finely divides and disperses the oxygenating air, thereby maintaining better and more efficient contact between the available air in the digesting mass and the microorganisms in the mass. If desired the direction of rotation of the turbine can be reversed to cause the fluid to flow in the opposite direction.

The fecal material must be digested at thermophilic digesting temperatures for a period of at least four days. After about eight days at thermophilic digesting temperatures, it has been found that the protein level in the digested product begins to fall. Thus the optimum range for protein production requires that the waste material be digested at thermophilic temperatures for a period of from four to eight days. It has also been found that after about five days at thermophilic digestion temperatures, no significant increase in the protein level of the digested product is obtained. Therefore it is preferred that the fecal matter be digested at thermophilic digestion temperatures for only about four to about five days. When the process of the present invention is conducted under batch conditions, that is, when the digestion process is initially started at ambient temperatures below thermophilic digestion temperatures, it normally takes about three to four days for the waste material to rise from ambient temperatures to the thermophilic range. Thereafter, it has been found that a four to five day residence time in the digester at thermophilic digestion temperatures produces the optimum foodstuff in the most economical manner.

Heretofore, the present invention has been described only by relation to a batch process wherein the digestion reaction is initiated on fecal matter that is at ambient temperatures. The present invention is also applicable to continuous digestion processes wherein a series of two or more digesters and preferably three are linked in a series fluid flow arrangement. The continuous reaction is initiated in a first digester of a series arrangement in a manner identical to that described in conjunction with the batch processes above. After the fecal matter in the first digester has reached thermophilic digestion temperatures, a portion of it is transferred to a second digester where it is allowed to digest for an additional period of time. At the same time, additional fecal matter can be added to the first digester without causing the temperature of the digesting mass in the first digester to drop below thermophilic digestion temperatures. The exact amount that can be continuously added to the first digester is of course dependent upon the particular thermophilic digestion temperature at which the digester is operating as well as the relative volumes of fecal matter in the digester and fecal matter being added. When the fecal material is digesting at temperatures above 55° C., additional quantities of fecal material on the order of 50% by weight of the digesting material in a given digester can be introduced into the first digester without adversely affecting the digesting temperature. However, it is important that if the temperature in the first digester is caused to drop below the thermophilic digestion temperature ranges by the introduction of too much additional fecal material, no more fecal material be added until the temperature has again risen to the thermophilic range. It has been found for a continuous digestion process that a residence time of the digesting material in the two or more digesters be maintained at from about four to eight days.

The digested product of the present invention, which largely comprises a brownish liquid, can be directly fed to animals. For example, the digested product of the present invention has been directly fed as a liquid to hogs, cattle, sheep and chickens. The protein content of the digested product is higher than that of the initial fecal material, indicating that cellular, proteinaceous organisms have been produced. It is believed that the protein present in the digested product is in the form of single cell microorganisms and other protein sources, which provide a very readily digestible energy and protein source for animals.

Alternatively to feeding the digested product to animals directly as a liquid, the liquid product can first be filtered to remove the solid material in suspension. This solid material can then be directly refed to animals. As a further alternative, this solid filtered material can be dried and the dry product fed directly to animals. The product thermophilically digested in accordance with the foregoing procedures has been filtered first through a 30-mesh screen and thereafter through a 150-mesh screen. The solid material left on the screens can be directly refed to animals. If desired, the solid material left on the screens can be dried by placing it on a drying platform or plate exposed to the air. The material can be air dried at ambient temperatures or can be heated to accelerate the rate at which moisture is driven from the solid material. This dried solid material can also be refed to animals. It has been found, however, that the nutrient quality of the solid material after the filtration process is not as high as the liquid digested product taken directly from the digester. This observation indicates that a substantial portion of the proteinaceous material produced by the digestion passes through the 150-mesh screen with the filtrate and is lost as a nutrient source when only the solid material is refed. Thus, the preferred form of the invention requires refeeding of the digested product in its whole liquid form. If the digested product is not fed in its whole liquid form, the solid material cannot constitute as large a proportion of the total nutritive diet for the animals as when the complete liquid digested product is directly fed. An additional advantage of drying the digested product is that it is stable and can be stored for long periods of time, on the order of several months, with no loss in its nutritive value.

It is to be emphasized that the thermogenic bacteria developed in accordance with the present invention are those that naturally occur in animal fecal matter and that are developed in accordance with the procedures heretofore described. It is believed that the genesis of the particular thermophilic bacteria that digest the waste matter at the thermophilic temperatures is a development through successive stages from the psychrophilic or mesophilic and possibly dormant thermophilic bacteria present in the fecal matter under ambient conditions. By properly aerating and agitating the animal fecal matter in accordance with the foregoing process, the bacteria developed through the successive stages to the thermogenic thermophilic bacteria accomplish the ends of the present invention. Attempts have been made to isolate and identify the particular thermophilic bacteria present in the digesting mass at the thermophilic digestion temperatures; however, no concrete identification of the strain or strains has been made at this point in time. It is to be further emphasized that no external heat input to the digesting mass is required for purposes of the invention as the bacteria naturally occurring in the fecal matter are thermogenic, that is they are responsible for the heat input to the digesting material to raise the temperature of the digesting material from ambient to thermophilic digestion temperatures and to maintain the material at those temperatures. Although a small amount of energy is added to the digesting mass via the mechanical action of the agitating mechanism on the fluid, the amount of energy supplied to and dissipated in the digesting mass as heat is small, and in fact, is insufficient per se to raise the temperature of the digesting mass more than a few degrees and is certainly insufficient to raise the temperature of the digesting mass to the thermophilic digestion temperatures. Thus the thermogenesis responsible for the success of the present invention is solely attributable to the metabolic activity of the bacteria naturally occurring in the fecal matter.

Although the thermophilic aerobic digestion process of the present invention has been thus far described in conjunction with the digestion of animal waste matter, it has been found that the process has much broader application than only to the digestion of fecal matter. The thermophilic thermogenic bacteria produced by thermophilically digesting animal fecal matter are also produced by digesting other biologically degradable organic materials in accordance with the procedures and within the limitations just described with respect to the fecal matter digestion. Included in the broad class of biodegradable organic materials that are digestable in accordance with the present invention are the carbonaceous solid wastes such as human wastes including sewage sludges, carbonaceous domestic and industrial wastes such as fruit and vegetable processing wastes, animal packing plant wastes, fish cannery wastes, and wood or woody materials. Other materials such as biodegradable garbage wastes, for example, fruit and vegetable peels, chicken feathers and the like can also be digested in accordance with the present invention. All of these materials can be digested utilizing the aforementioned thermophilic thermogenic bacteria into single cell proteinaceous material suitable for feeding to animals as a nutrient source.

The process for digesting the organic biodegradable materials mentioned above can be initiated in at least four ways. First, these biodegradable materials can be digested in accordance with the present invention by merely placing them in a suitable digester and aerating and agitating and otherwise processing the materials within the conditions and bounds described above in relation to the digestion of fecal matter. Secondly, the biodegradable materials can be digested in accordance with this broad aspect of the present invention by combining them with animal fecal matter or other waste matter containing a microbial population of sufficient composition to raise the temperature to and maintain the temperature of the mixture at thermophilic conditions and aerating and agitating within the critical limits described above in relation to digestion of animal fecal matter alone. Thirdly, the biodegradable materials can be added to digesting fecal matter after the temperature of the digesting fecal matter has been raised to thermophilic digestion temperatures in accordance with the present invention. Fourth, the biodegradable materials can be combined with water to form an aqueous slurry. Thereafter, the inoculum obtained from an organic material that is thermophilically digesting in accordance with the invention can be introduced into the aqueous slurry. Agitation and aeration of the aqueous biodegradable slurry can then be initiated in accordance with the critical parameters set forth above in relation to digestion of animal fecal matter.

It is to be recognized that once the thermophilic thermogenic bacteria of the present invention have been developed by processing animal fecal matter or other organic biodegradable materials in accordance with the present invention, it is necessary only to add nutrients for the bacteria to the digesting mass. Thus, once the thermophilic digestion temperatures have been achieved, additional biodegradable material can be added on a continuous basis to the digesting mass. The process can then be continued for as long a period as desired. Once the biodegradable material is digesting at thermophilic temperatures in accordance with the invention, additional biodegradable material can be added to the digesting zone in amounts up to a quantity that will cause a reduction in the temperature of the animal fecal matter below the thermophilic digestion temperature range.

When the thermophilic aerobic digestion process of the present invention is initiated with biodegradable material other than animal fecal matter, water must often be added to the mixture to form an aqueous slurry. To initiate the thermophilic digestion process of the present invention from ambient temperatures, the dry solids content of the biodegradable material based on the entire aqueous slurry must be at least about 5% by weight. Preferably, the biodegradable material can be present in the aqueous slurry in amounts up to 15% to about 20% by weight, although an excessive amount of solid material in the aqueous slurry will greatly increase its viscosity and thus increase the energy required for adequate agitation in accordance with the present invention. After the aqueous slurry is introduced into the digester, aeration and agitation are begun and are maintained within the parameters described above in relation to the animal fecal matter digestion. The temperature of the aqueous slurry will begin to rise and will achieve thermophilic digestion temperatures. By continuing the agitation and aeration at the prescribed critical rates, the thermophilic digestion temperatures can be maintained.

As stated above, the thermophilically digested product from biodegradable organic material in accordance with the foregoing broader aspects of the present invention can be utilized as animal feed. Some industrial processing wastes such as byproducts from fruit or vegetable processing plants, may contain a higher degree of carbohydrate nutrient than animal waste matter. The process of the present invention breaks down the biodegradable material into a form that is readily digestible by animals. The nutrient value of the digested product must be analyzed and must be supplemented to make up a complete nutritive diet for a given animal or animals.

Indiscriminate feeding of all digested biodegradable materials cannot be done since some of the biodegradable materials, for example, sewage sludges, contain substances that may not be digestible by the thermophilic thermogenic bacteria and moreover may not be digestible by animals. Such substances included in sewage sludges are glass, plastics and metals. If such substances are present in the organic biodegradable materials at levels below that which would be toxic to animals, it may still be possible to feed the digested product to animals.

As in the thermophilic digestion of animal fecal matter in accordance with the present invention, the digestion of organic biodegradable materials will produce a protein increase over that of the material introduced into the digesting zone. Again, the protein increase is believed to be caused by an increase in the microbial population during digestion, resulting in an increase in single cell proteinaceous material, that is, single cell protein derived from the microbial biomass present in the digested product. As with the digesting animal wastes, protein production is at its maximum after about four to eight days of digesting at the thermophilic digestion temperatures. After about eight days of digesting at the thermophilic digestion temperatures, the protein content of the digested product begins to decline. It is therefore preferred when the digested product is to be fed to animals that the digestion process be operated at thermophilic digestion temperatures only for a period of from about four to about eight days.

It is recognized however, that the thermophilic digestion process of the present invention can be continued for periods beyond eight days. If the thermophilic digestion process is continued for a longer time, a significant reduction in the biological oxygen demand (BOD) is achieved after about six days, while the greatest BOD reduction is achieved after about seventeen days of digesting at thermophilic digestion temperatures in accordance with the invention. A reduction in the chemical oxygen demand (COD) is also achieved while digesting biodegradable material in accordance with the invention. A significant COD reduction has been achieved after about eleven days of digesting at thermophilic digestion temperatures while a significant reduction in COD has been obtained after about twenty-four days of digesting at thermophilic digestion temperatures. An unexplained rise in COD has been observed within the period of from eleven days to about twenty-four days. This rise in COD is thought to be attributable to the increase in cellulose content as a percentage of total solids, as the solids other than cellulose are being digested at a faster rate than the cellulose cells. After twenty-four days, however, both the BOD and COD are reduced significantly and sufficiently so that the digested product can be used as a fertilizer or can be disposed of relatively safely and economically. Also, when sewage is used as the starting waste material, the digested product will contain additional amounts of plant nutrients such as phosphorous and nitrogen.

If it is desired to completely stabilize a biodegradable material such as sewage sludge by the process of the present invention, relatively complete stabilization can be achieved by continuing the thermophilic digestion process of the present invention until the temperature of the digesting material drops below the thermophilic digestion temperature range. When this occurs, a completely stabilized digested product is obtained. With heavy solids concentrations in the digesting mass time periods in excess of fourteen days may be required for complete stabilization.

Surprisingly, it has also been found in accordance with yet another aspect of the present invention that the thermophilic, thermogenic bacteria produced by digesting animal waste matter or other biodegradable material in accordance with the present invention are also effective to digest lignocellulosic compounds or materials. Such materials include the woody plants, such as trees, shrubs and wood refuse, and the byproducts of wood processing industries. Although there are certain fungi that will digest the lignin present in lignocellulosic materials over a relatively long time, on the order of 100 years or more, heretofore, microbiological digestion processes have not been capable of digesting lignocellulosic materials in any reasonable length of time.

By adding lignocellulosic materials in coarsely divided form to a digester containing animal fecal matter digesting at thermophilic temperatures in accordance with the foregoing described invention, it has been found that in a matter of hours the digestion process begins to break down the lignin in the lignocellulosic materials and free cellulose cells for digestion, and that in four to five days, the lignocellulosic materials are substantially digested. More surprisingly, however, it has been found that the procedures of the present invention are effective to digest lignocellulosic material in coarsely divided form in the absence of fecal matter or other biodegradable material. That is, lignocellulosic material can be combined with water to form an aqueous slurry. Thereafter upon appropriate aeration and agitation in accordance with the procedures outlined above for animal waste matter and other biodegradable material, lignocellulose materials can be digested. Initial aeration and agitation produces thermogenic bacteria which raise the temperature from ambient temperatures to the thermophilic temperature range on the order of 55° C. or higher. Thereafter, the thermophilic thermogenic bacteria continue to digest the lignocellulose material. Similar to when the lignocellulosic material is added to already thermophilically digesting animal waste matter or other biodegradable material, the lignocellulose material when digested in the absence of other biodegradable material will also be partially digested within 4 to 5 days after the thermophilic digestion temperatures are reached.

It is preferred that the lignocellulosic materials be coarsely comminuted by chipping or other convenient methods to increase the surface area over which the microorganisms can attack. Coarsely comminuted materials include sawdust (having a mean particle size on the order of 1/32" in diameter or larger) or wood chips (having an average particle size of on the order of 0.2×0.2×0.2 inches). It is not necessary, however, to finely divide or comminute the material to a dust or flour-like consistency in order for the present invention to be operable. The lignocellulosic material can be present in the digesting mass in amounts up to about 50% by weight of the digesting mass. When amounts of lignocellulosic material approaching 50% by weight are employed, however, the power requirements for agitation rise significantly. It is therefore preferred that the amount of lignocellulosic material present in an aqueous digesting medium be maintained below about 15% by weight of the total digesting mass to minimize agitation power requirements.

The lignocellulosic materials can also be combined with water and a relatively small amount of animal fecal material in a digester to accelerate the digestion process. Preferred proportions are about 3.5% to 5% by weight of animal fecal material, about 2% to about 8% of lignocellulosic material, and from 87% to about 94.5% by weight of water. When a mixture falling within the foregoing proportions is placed in a digester and the mixture is aerated and agitated in accordance with the procedures outlined above in connection with the digestion of animal fecal matter the naturally occurring microorganisms in the animal fecal matter will cause the temperature to rise in a manner very similar to that when fecal material or lignocellulosic material alone is present in the digester. By continuing the vigorous agitation and aeration in accordance with the above procedures, thermophilic digestion temperatures are achieved in a matter of about four days. By maintaining these thermophilic digestion temperatures for a period of at least four days up to twenty-one days or more in accordance with the procedures outlined above, the lignocellulosic materials can be completely digested.

It is evident that lignin from the lignocellulosic material is being digested in accordance with the present invention, as a scum appears on top of the digesting lignocellulosic material after a few hours of digestion. The scum is comprised of free cellulose cells from which the lignin has been substantially removed. These cellulose cells are in a form that can be digested by animals without further digestion in accordance with the present invention. If desired, however, the digestion process can be continued after substantially all of the cellulosic cells are freed so that a portion or all of the cellulosic cells are also digested to produce single cell protein and other nutrients for animals.

The process of the present invention wherein lignocellulosic materials are digested can also be operated either on a batch basis or on a continuous basis. The same process parameters apply to the lignocellulosic digestion as to the digestion of animal fecal matter and other biodegradable material, especially the critical nature of the aeration and agitation.

It is believed that the genesis of the thermophilic bacteria that digests the lignocellulosic materials is a successive development of a certain strain or strains of bacteria through thermophilic, thermogenic, aerobic digestion process of animal fecal matter or other organic materials containing organisms of similar capability, as described above. A sample culture taken from a thermophilically digesting mass, in which the starting material was animal fecal matter, namely hog manure, and to which lignocellulosic materials were added after thermophilic digestion temperatures were reached, has been extracted from the digesting mass. The culture has been deposited with the American Type Culture Collection, 12301 Parklawn Drive, Rockville, Maryland 20852. The culture has been given Accession Number ATCC-31205 by the American Type Culture Collection. Access to the culture will be available during pendency of the patent application to one determined by the Commissioner to be entitled thereto under 37 CFR 1.14 and 35 USC 122. Further, all restrictions on the availability to the public of the culture so deposited will be irrevocably removed upon the granting of a patent hereon. The applicants hereof assure permanent availability of the culture to the public through the American Type Culture Collection. The best description of the culture and taxonomy avaiable at this time follows.

The thermophilically digesting liquid in which alder wood chips were being digested yielded a mixed culture of thermophilic organisms when cultured in modified trypticase soy agar. The modification to the agar included the addition of 0.4 gm/l. of yeast extract and three additional grams of Agar per liter. One-tenth (0.1) ml/l. of concentrated ammonium hydroxide was added after sterilization of the medium. The growth medium had a final pH of approximately 7.5. The culture time in this medium was 24 hours. The organisms were separately cultured to both 55° C. and 75° C. on the medium or in its broth. Four organisms were observed.

The first organism was a gram negative rod having a length of from 0.7 to 1.7 microns and a diameter of 0.3 microns in the broth. The organism had spores, namely an endospore 1.4 microns long and 0.7 microns wide. The first organism grew only at 55° C. and did not grow at 75° C. The organism was a vegetative cell. Under phase contract microscopy the organism showed definite, dark, granular-like bodies and had no motility. The colony of the first organism had a creamy white color and was opaque. The colony elevation was umbonate while the colony edge was between crenate and undulate.

The second organism was filamentous. The filaments were gram negative and contained gram positive granules. The organism was not a typical bacillus form but tended toward long filaments. The organism grew slowly at 75° C. while excellent growth was obtained at 55° C. The colony was light brown in color. The colony elevation was umbonate. The colony edge was lobate over its entire surface.

The third organism in the broth medium was observed to be gram negative bacillus-type rods. The rods were from 2.1 to 3.5 microns in length and 0.5 microns in width. The rods tended to bend in the center to form "U" or pretzel shapes. The rods had a cytoplasmic spherical mass at the bend. The culture also contained numerous large, ball-shaped bodies containing what appeared to be small rods shaped much like small rod-shaped bacilli.

On the solid media, the third organism was observed to be gram negative, highly filamentous rods. The rods were straight or curved. Some of the filaments were observed to form loops, some of which contained spherical shapes observed in the broth culture. The colony was cream colored and was opaque. The colony elevation was convex while the colony edge was entire. The third organism grew at 75° C. in both the broth and the solid media while very little growth was observed at 55° C.

The fourth organism was a bacillus-type gram negative rod. The rod length varied from 2.4 microns to 35 microns with most rods being about 4.5 microns in length. The diameter of the rods was about 0.5 microns. A few filaments were observed up to 100 microns in length. The rods were generally straight. Some of the rods tended to have pointed ends and some of the rods were slightly curved. The colony was light brown in color and was opaque. The colony elevation was convex and the colony edge was entire.

In accordance with another aspect of the present invention it has been found that vitamin $B_{12}$ can be extracted from the digested product formed from the fecal matter digested in accordance with the present invention. The vitamin $B_{12}$ can be separated from the digestion product by various procedures known in the art, including the methods outlined in the "Association of Official Analytical Chemists" (11th Edition), Washington, D.C. Vitamin $B_{12}$ can also be extracted from the digested product of other biodegradable materials digested in accordance with the invention, such as food plant wastes, wood wastes and many biodegradable organic wastes, as vitamin $B_{12}$ is produced as a function of the particular bacteria involved, and is not produced as a characteristic of the waste material.

Also in accordance with the present invention, amino acids and antibiotics can be produced. Amino acids are produced by seeding the digesting mixture of any of the foregoing biodegradable materials once thermophilic temperatures have been reached with organisms that have a high natural content of amino acids such as lysine and methionine. The digestion process over a period of 3 to 4 days evolves into a mass containing high levels of lysine. Once the mass has been digested for a period of on the order of 4 days or more, the digested product can be fed to animals to meet their requirements for lysine, methionine, and other selected amino acids. Similarly, organisms high in lysine or other amino acids can be seeded into the digesting mass as it is being brought through the mesophilic range from ambient temperatures. By the time thermophilic temperatures are reached, the microorganisms high in lysine or other selected amino acid would be the dominant species in the digesting mass. Of course, when purified, digested products containing amino acids would also be available for human consumption.

Also in accordance with the present invention, it is within the purview of the invention to produce sugars and lignin from the breakdown of the lignocellulose bonds in wood products. The simple sugars thus produced can be used for commercial purposes, e.g., for fermentation to produce alcohol. The lignin fraction can be used in the feeding to ruminants as at least a portion of the fiber portion of their diet. The sugars so produced are also utilizable by ruminants and other animals.

EXAMPLES

The following examples are intended to be illustrative of the present invention and are not intended in any way to be delimitative of the broader concepts disclosed herein. The examples are further intended to teach one of ordinary skill how to make and use the invention and how to produce the results of the invention.

In all of the following Examples, a cylindrical digesting tank having a diameter of 48 inches and a height of 5 feet was placed upright on a foundation. The top of the tank was open to the atmosphere. A 1 inch thick layer of insulation surrounded the sides and the bottom of the tank. The insulation was a closed cell polyurethane foam material. A 0.5 inch diameter aerating pipe was routed to the bottom of the tank and had its outlet positioned substantially along the axis of the tank about 6 inches above the bottom of the tank. Oxygenating air was fed through the pipe from a compressed air source. A volume regulating valve was interposed between the air compressor and the outlet from the aerating pipe. A four bladed impeller was mounted on a rotatable shaft oriented coaxially with the tank. The four impeller blades were positioned 90° apart and had their longitudinal dimension oriented radially on the rotatable shaft. The blades were 3 inches long in radial dimension and 6 inches long in the transverse dimension. The blades were oriented at 30° to the horizontal, i.e., to the bottom of the tank. A 2 H.P. electric motor was mounted on a platform resting on the upper edges of the sides of the tank and coupled to drive the rotatable shaft at 860 rpm. The shaft was driven in a direction so the digesting material in the digester would be driven upwardly from the bottom of the tank, through the blades and on upwardly to the upper surface level of the material in the tank. The bottom of the impeller was positioned 2 inches above the outlet from the aerating pipe so that air issuing from the aerator pipe traveled upwardly through the rotating impeller blades. The shearing action of the blades on the airstream better dispersed the air throughout the liquid to achieve a higher dissolved oxygen content in the liquid. A foam beaker was also mounyted on the platform resting on the top edges of the side walls of the tank. The foam beaker consisted of four blades positioned 90 degrees apart on a rotating shaft driven at 1725 rpm by a ¼ H.P. electric motor. The blades were 6 inches long and were positioned at a level of 6 inches above the surface of the digesting liquid. The foam beaker was offset from the impeller shaft so as not to interfere with its operation.

EXAMPLE I

Water was added to hog manure washed from hog feeding platforms and stored in a holding tank. The hog manure was about 10 days old when it was introduced into the digester. The manure had a dry solids content based on the total aqueous mixture introduced into the tank of about 10% by weight. The ambient temperature was 10° C. when the aqueous mixture was introduced into the digester. Immediately after the mixture was introduced into the digester, oxygenating air was pumped into the digester at the rate of 0.02 liters of air per minute per liter of aqueous mixture in the digester. At the same time, the impeller was started. Aeration at this rate and agitation at this level were continued throughout the run until immediately before the digested product was removed from the digester. Within 6 hours, the temperature began to rise from the ambient and within 90 hours, the temperature was at 55° C. During the initial start-up phase when the temperature was rising to the thermophilic digestion temperatures, foam was produced on the top of the aqueous mixture. The foam breaker was adjusted so that the foam layer was maintained at about 8 to 12 inches thick. The foam layer served as insulation to prevent heat loss from the top of the tank.

The aqueous mixture was digested at thermophilic temperatures for 6 days. During this 6 day period, the temperature remained at thermophilic digestion temperatures in the range of from 55° C. to about 65° C. During this time the dissolved oxygen levels were maintained within the range of from 1.5 mg/l. to 3 mg/l.

At the end of the 10 days after initiation of the digestion process, the digested product was removed from the digester and soon thereafter fed to hogs as 10% of their total nutritive diet with no adverse effects. The balance of the diet of the hogs was normal feed supplement and grains normally fed to 24 test hogs.

The foregoing process was repeated over a period of 28 days so as to produce a sufficient amount of liquid, digested product to provide a constant supply of the material sufficient to feed to test hogs for 28 days. The liquid product was fed to the hogs on an ad libitum basis as the only source of liquid, i.e., in the place of water, and constituted about 30% of their daily protein requirements. After the 28 day period, the hog weight gain and feed conversion efficiency were substantially the same as an identical number of control hogs fed a totally fresh diet of feed supplement and grain identical to that making up the remainder of the nutritive diet of the test hogs. Feed conversion efficiency is defined as the inverse ratio of the amount of feed required to produce one pound of meat times 100%.

The digested product was analyzed and found to contain single cell proteinaceous material. The amino acid profile of the digested product was derived in accordance with common laboratory procedures. The amino acid profile of the digested material compared with the amino acid profile of the original hog manure placed in the digester indicates that a significant increase, on the order of 100%, in several of the amino acids is achieved by digesting the hog manure in accordance with the present invention.

EXAMPLE II

The process of Example I was repeated with chicken manure to which water was added to adjust the dry solids content to about 12% by weight based on the total aqueous mixture. When the digestion was begun, the ambient temperature was about 12° C. After the aeration and agitation were begun, the temperature of the digesting material rose to 55° C. in about 72 hours. The temperature was maintained in the range of from 55° C. to 78° C. by continuous agitation and aeration for 12 days. The dissolved oxygen levels in the digesting material were maintained in the range of about 1 mg/l. to about 3 mg/l. after 12 days, the digested product was removed from the digester and fed to 340 test chickens as between 5% and 15% of their total nutritive diet. No adverse effects were observed. The test chickens' weight gain and feed conversion efficiency were substantially the same as the same number of control chickens fed a totally fresh diet identical to that making up the remaining 85% to 95% of the diet of the test chickens.

EXAMPLE III

The digestion process of Example I was repeated and allowed to continue digesting for a period of three weeks, while the aeration and agitation were continued. During that period the temperature of the digesting material reached 74° C. and then dropped to 60° C., indicating that the nutrient source for the microorganisms was being depleted. At the end of the three week period, 3 Kgs. of alder chips were added to the digesting mixture. The agitation and aeration was continued. The average chip size was approximately 0.5 mm by 0.5 mm by 4 mm. Within 24 hours after the chips were added, the temperature of the digesting mixture had risen to 64° C. Thereafter 3 to 4 Kgs. of alder chips were added to the digester every two to three days while agitation and aeration were continued. After approximately two weeks, digestion of the alder chips was noted. For approximately one week thereafter, no new chips were added to the digester, during which period the pH of the digesting liquid rose from about 7.0 to about 8.8, accompanied by a strong ammonia smell from the digester. 10 Kgs. of alder chips were then added to the digester. Within 12 hours thereafter, the pH of the digesting liquid had dropped to 7.0 and there was no further ammonia smell. The alder chips were digested within 21 days after the initial batch was introduced into the digester to an extent that no discrete chip particles remained in the digesting material. A total of 100 Kgs. of alder chips were periodically added over a period of 118 days with no further addition of hog manure or other nutrients. After the chips were digested, the digested material was removed from the digester and fed to 15 hogs with no adverse results as a portion of the total nutritive diet of the hogs. The cellulose cells, after being removed from the digester, are in a form that can be digested by animals, especially ruminants.

When following the procedure of the foregoing Example III, it will be noted that when addition of alder chips at regular intervals was stopped, after about one week the pH of the digesting mass rose significantly into the alkaline range. In addition, an ammonia smell was observed indicating that ammonia was being generated in the digesting mass. These observations indicate that nitrogen fixation was taking place in the digesting mass at temperatures of from 64° C. to about 67° C. Heretofore, it has been thought that nitrogen fixation could not occur above about 40° C. The explanation for the nitrogen fixation is presently uncertain. It is also to be observed that when additional lignocellulosic material is added to the digesting mass, the pH will very soon thereafter drop to about 7.0. This same phenomenon has been observed in extended digestion of animal fecal matter and other carbonaceous materials, that is, after the digesting mass is allowed to digest at thermophilic temperatures and is aerated and agitated in accordance with the invention, the pH will tend to rise several days after the last carbonaceous material was added. Upon adding new carbonaceous material, a pH drop as been observed.

The starting material was analyzed and found to contain 0.2496% nitrogen on a dry weight basis. Nine samples of the digested product were taken from the digester at intervals during the 118 day period and were analyzed for nitrogen. The average nitrogen content of the nine samples was 3.968% on a dry weight basis. The crude protein content of the original material and digested product is calculated by multiplying the nitrogen content by 6.25. Thus, the original material contained 1.56% crude protein on a dry weight basis. The average crude protein content for the nine samples was 24.8% on a dry weight basis. This increase in crude protein clearly shows that nitrogen from the atmospheric air supplied to the digestion process was "fixed" in the end product, that is, converted to usable protein, since no material was added to the digester other than the wood and domestic tap water.

EXAMPLE IV

The process of Example I was repeated, except that several pounds of fruit peels, chicken feathers, newspapers and other carbonaceous garbage were introduced into the digester after the temperature reached 60° C. All of the garbage was digested at temperatures ranging from 55° C. to 75° C. The digested product was fed to hogs as a portion of their nutritive diet without adverse effects.

As can be observed by reading the foregoing specification, the objects set forth above have been achieved. The thermophilic aerobic digestion process of the present invention produces a foodstuff that can be refed to animals as a portion of their nutritive diet. When the critical levels of aeration and agitation are maintained in accordance with the present invention, no external heat need be added to the digesting material to raise its temperature to the thermophilic temperature range or to maintain the digesting material within that temperature range for a period of on the order of four days or more. Inoculation of the fecal material to be digested is not required as microorganisms naturally occurring in the animal fecal matter are adequate to achieve the foregoing results. Moreover, the process of the present invention produces single cell proteinaceous material and yields an end product having a protein content in the digested product equal to or greater than that present in the original fecal materials introduced into the digester. Moreover, the equipment necessary to practice the present invention is relatively simple and requires little capital investment to construct or maintain, and little operating expense to conduct the digestion process.

EXAMPLE V

The procedure of Example I was repeated except that bovine animal manure was employed as the biodegradable material. Once the digesting mass had reached thermophilic temperatures and digested at thermophilic temperatures for a period of four days, a sample of 10 milliliters of the digestion product was taken. The sample was blended with 250 milliliters of a metabisulfite extraction buffer and diluted to one liter with distilled water. The solution was thoroughly mixed and then autoclaved at 121° C. for a period of 10 minutes to extract the vitamin $B_{12}$ from the sample. The experimental extraction procedure followed is the method outlined by the Association of Official Analytical Chemists (11th Edition), Washington, D.C. Vitamin $B_{12}$ was yielded in an amount of 0.3 mg/l. of the digested bovine animal manure.

EXAMPLE VI

The procedure of Example V was repeated with poultry manure. The assay yielded 0.16 mg/l. of vitamin $B_{12}$.

EXAMPLE VII

A mixture of water and alder chips was introduced into the digester. Approximately 7 kilograms of alder chips were used; the alder chips constituted approximately 12.5 percent by weight of the total mass introduced into the digester. The alder chips were approximately 0.5 mm×0.5 mm×4 mm in size. The initial crude protein content of the alder chips was about 1.56% by weight before digestion. The ambient temperature was on the order of 8° C. When the aqueous mixture was introduced into the digester. Immediately after the mixture was introduced into the digester, oxygenating air was pumped into the digester at a rate of 0.02 liters of air per minute per liter of aqueous mixture in the digester. At the same time the impeller was started. Aeration at this rate and agitation at this level were continued for a period of seventeen weeks. Within 12 hours after the impeller was started and aeration begun, the temperature of the mixture began to rise from ambient and within $13\frac{1}{2}$ days, the temperature had reached 74° C. During the initial start-up phase when the temperature was rising to the thermophilic digestion temperatures, some foam was produced on the top of the aqueous mixture. However, no foam breaker was necessary to reduce the thickness of the foam layer.

EXAMPLE VIII

The procedure of Example I was repeated with the exception that potato waste was employed instead of animal fecal matter. The potato waste comprised potato peels and adjacent potato material discarded by a potato processing factory. The potato waste had a crude protein content of about 9% on a dry weight basis. The potato waste had been taken from the raw potatoes from 0 to 7 days prior to its introduction into the digester. Water was added to the digester to bring the total solids content in the digester up to about 8.3 percent on a dry weight basis. Thermophilic digestion temperature of 50° C. were achieved within 64 hours after beginning the agitation and aeration in accordance with the present invention. Thermophilic digestion was continued for a period of about 16 days. At the end of the 16 day period, the digested product was analyzed for crude protein and was found to contain about 25 percent protein on a dry weight basis.

EXAMPLE IX

The procedure of Example VII was repeated after the mass had digested at thermophilic temperatures for a period of 20 days, a sample of the digestion product was taken. The sample was found to contain certain enzymes that were capable of readily attacking and degrading the cellulose in the lignocellulosic material. These enzymes were isolated and identified as cellulase in accordance with the procedures outlined in Sumner and Somers, Laboratory Experimentation, Biological Chemistry, Academic Press, New York, p. 34.

An aliquot of the digested material was taken from the digester and was centrifuged to separate the solid material. To one (1) ml. of the remaining liquid was added one (1) ml. of carboxymethylcellulose reagent. The resulting mixture was incubated at 40° C. for one hour. Two (2) ml. of dinitrosalicylic acid were then added to the incubated mixture. The reduction rate of sugars was then measured. Six-tenths (0.6) mg. of reduced sugars per minute per ml. of enzyme solution was obtained. It must be noted that the foregoing determination was conducted at the pH of the digested material (approximately pH 8). Since cellulase functions best at a pH on the order of 4.4, it is clear that the sugar reduction rate would have been higher had the determination been conducted at the lower pH.

In its broadest aspects the thermophilic digestion process of the present invention can be employed to break down organic biodegradable materials to either reduce them to a readily digestible form and to produce protein or to stabilize the materials for disposal. The digested product can be fed to animals, thereby taking advantage of the nutrient value in waste products such as those normally disposed of in animal processing plants and fruit and vegetable canneries. Moreover, biodegradable wastes such as sewage sludges and the like can be completely stabilized by conducting the thermophilic digestion process of the present invention to a point where there is no longer sufficient nutrient for the thermophilic thermogenic bacteria to digest. The resulting product thus digested is completely stabilized and can be disposed of in a safe and economical manner. In all cases the digestion process of the present invention does not require addition of external heat to the digesting zone. Instead, by proper aeration and agitation in accordance with the present invention, the thermogenic nature of the bacteria present in animal fecal matter is relied upon to both raise the temperature of the digesting materials to the thermophilic range and to maintain the thermophilic digesting temperatures for periods of at least four days and longer.

An unexpected and important aspect of the present invention provides a process for microbiologically digesting lignocellulosic materials under aerobic, thermophilic conditions. Not only does the process of the present invention digest the lignocellulosic materials, but it does so in a relatively short time, on the order of four to eight days. The digestion process of the present invention reduces the lignocellulosic materials to a form that is readily digestible by animals. This process provides a source of additional nutrient for animals heretofore unavailable, as prior chemical pulping processes for removing lignin from a lignocellulosic material yield products and byproducts that are not acceptable for feeding to animals. The significant advantage of the present process for dissolving the lignocellulosic materials is that the end product does not contain the chemical contaminants normally yielded as a byproduct of the chemical pulping processes. Other important aspects of the present invention include protein production utilizing atmospheric nitrogen and production of enzymes and amino acids.

The foregoing invention has been described in relation to preferred embodiments as well as defining the broad operational parameters of the invention. One of ordinary skill, after reading the foregoing specification, will be able to effect various changes and substitutions of equivalents, and find additional uses for the invention without departing from the broad concepts disclosed herein. For example, the digested product produced by the present invention as disclosed is intended for animal consumption, the product may also be fit for human consumption. All indications at this point in time are in that direction; for example, the digested product is non-toxic, is odorless, is tasteless, and has an increased protein content over that of the undigested material. It is therefore intended that the Letters Patent granted hereon be limited only by the definitions contained in the appended claims and the equivalents thereof.

The embodiments of the invention in which an exclusive property or privilege is claimed are as follows:

1. A process for using thermophilic bacterial microorganisms for thermophilically digesting an aqueous mixture of at least one material selected from the group consisting of animal fecal matter, lignocellulose and vegetable matter under aerobic conditions consisting essentially the steps of:
introducing said mixture into a digester that is sufficiently insulated to prevent substantial heat loss therefrom,
continuously introducing air into said mixture while continuously, mechanically and vigorously agitating said mixture, said air being introduced at a rate sufficient to maintain the dissolved oxygen level in said mixture above about 0.2 mg/l. and said mixture being vigorously agitated at a level effective to cause and promote the temperature of said mixture to rise from ambient temperatures, through mesophilic temperatures, to a temperature of at least 55° C. without the addition of external heat to said mixture until said material is digested, said mixture when digested forming a digested product, said air further being supplied at a rate sufficient to maintain a dissolved oxygen level in said mixture effective to supply the biological oxygen demand of the mixture,
continuing to agitate said mixture at a level and to introduce said oxygenating gas at a rate effective to maintain said temperature of at least 55° C. without the addition of external heat, said oxygenating gas being introduced at a rate sufficient to raise the dissolved oxygen level in said mixture to and maintain it above about 1.0 mg/l. after the temperature of said mixture has reached 55° C.

2. The process of claim 1 wherein said oxygenating gas is introduced at a rate sufficient to maintain the dissolved oxygen level in said mixture between about 1.0 mg/l. and the oxygen saturation point of said mixture after the temperature of said mixture has reached 55° C.

3. The process of claim 2 wherein said oxygenating gas is introduced at a rate sufficient to maintain the dissolved oxygen level of said mixture between about 1.0 mg/l. and about 4.5 mg/l. after said mixture has reached 55° C.

4. The process of claim 3 wherein said oxygenating gas is introduced at a rate sufficient to maintain the dissolved oxygen level of said mixture between about 2.0 mg/l. and about 3.0 mg/l. after said mixture has reached 55° C.

5. The process of claim 1 wherein said air is continuously introduced into said digester at a rate of from about 0.01 liter to 0.02 liter of air per minute per liter of mixture.

6. The process of claim 1 wherein said mixture is agitated at a rate sufficient to permit the microorganisms in said mixture to contact oxygenating gas at least once every two and one-half minutes.

7. The process of claim 1 wherein said mixture is maintained at a temperature of at least 55° C. for a period of at least 4 days.

8. The process of claim 1 wherein said mixture is agitated and said air is introduced adjacent the bottom of said digester.

9. The process of claim 1 wherein said digester comprises a digesting tank having sides and a bottom and an open top and wherein said digesting tank is insulated by placing a layer of insulating material on the sides and bottom of said digesting tank, said introduction of oxygenating gas being in an amount sufficient to produce a foam layer on the top of the mixture, whereby the top of said mixture is insulated by maintaining said layer of foam on said mixture.

10. The process of claim 9 wherein said mixture is agitated by placing a rotating impeller adjacent the bottom of said digesting tank, said air being introduced into said digesting tank adjacent the bottom of said impeller and below said impeller, said air thereby being dispersed into a moving fluid stream in said digesting tank.

11. The process of claim 1 further comprising feeding said digested product to said animals as a source of single cell protein.

12. The process of claim 1 further comprising the step of extracting vitamin $B_{12}$ from said digested product.

13. The process of claim 1 further comprising the steps of:
after the temperature of the mixture has reached at least 55° C., adding at least one material selected from the group consisting of animal fecal matter, lignocellulose and vegetable matter to said mixture,
continuing to agitate said mixture at a level and to introduce said air at a rate effective to maintain the dissolved oxygen level in said mixture at at least about 1.0 mg/l. and to maintain the temperature of said mixture above about 55° C.

14. The process of claim 1 or 13 wherein the agitation and aeration is continued to produce a digested product comprising single cell protein from said lignocellulose material.

15. The process of claim 14 wherein said single cell protein is fed to animals as part of their nutritive diet.

16. The process of claim 14 wherein said single cell protein contains a greater amount of fixed nitrogen in the form of crude protein than does the lignocellulose material introduced into said mixture.

17. The process of claim 14 wherein enzymes that degrade lignocellulose material comprise a portion of the digested product, the process further comprising the step of extracting said enzymes from said digested product.

18. The process of claim 1 further comprising the step of
seeding the material with organisms that produce substantial amounts of amino acids, and agitating and aerating so as to promote the growth of said organisms, thereby yielding a digested product comprising amino acids.

19. The process of claim 18 wherein said organisms are seeded into said material when the temperature thereof is in the mesophilic range.

20. The process of claim 18 wherein said organisms are seeded into said material after the temperature thereof has reached 55° C.

21. The process of claim 18 wherein said organisms produce lysine.

22. The process of claim 18 wherein said organisms produce methionine.

23. A process for thermophilically digesting materials containing a lignocellulose material consisting essentially of the steps of:
mixing a coarsely divided lignocellulose material with water to form a slurry having a dry solids content of at least about 5% by weight based on the total mixture, introducing said slurry into a digester that is sufficiently insulated to prevent substantial heat loss therefrom, inoculating said slurry with a bacterial inoculant taken from a mixture containing animal fecal matter digesting at thermophilic temperatures, continuously introducing air into said slurry while continuously, mechanically and vigorously agitating said slurry, said air being introduced at a rate sufficient to maintain the dissolved oxygen level in said mixture above about 0.2 mg/l. and said slurry being vigorously agitated at a level effective to promote and raise the temperature of said mixture from ambient temperatures, through mesophilic temperatures, to at least about 55° C. and to maintain the temperature of said mixture at at least 55° C. without the addition of external heat until said lignocellulose material is substantially digested thereby to form a digested product, said air being supplied at a rate sufficient to maintain a dissolved oxygen level in said mixture effective to supply the biological oxygen demand of the slurry before the temperature of said mixture reaches 55° C. and at a rate sufficient to maintain the dissolved oxygen level in said mixture above about 1.0 mg/l. after the temperature of said mixture reaches 55° C.

24. The process of claim 23 wherein the agitation and aeration is continued to produce a digested product comprising single cell protein from said lignocellulose material.

25. The process of claim 24 wherein said single cell protein is fed to animals as part of their nutritive diet.

26. The process of claim 24 wherein said single cell protein contains a greater amount of fixed nitrogen in the form of crude protein than does the lignocellulose material introduced into said mixture.

27. The process of claim 24 wherein enzymes that degrade lignocellulose material comprise a portion of the digested product, the process further comprising the step of extracting said enzymes from said digested product.

28. A process for thermophilically digesting materials containing a lignocellulose material consisting essentially of the steps of:

mixing a coarsely divided lignocellulose material with water to form a slurry having a dry solids content of at least about 5% by weight based on the total mixture, introducing said slurry into a digester that is sufficiently insulated to prevent substantial heat loss therefrom, inoculating said slurry with a bacterial inoculant consisting essentially of a culture having the identifying characteristics of deposited strain ATCC 31205 deposited at the American Type Culture Collection, continuously introducing air into said slurry while vigorously agitating said slurry, said air being introduced at a rate sufficient to maintain the dissolved oxygen level in said mixture above about 0.2 mg/l. and said slurry being vigorously agitated at a level effective to promote and raise the temperature of said mixture from ambient temperatures, through mesophilic temperatures to at least about 55° C., and to maintain the temperature of said mixture at at least 55° C. without the addition of external heat until said lignocellulose material is digested, thereby to form a digested product, said air being supplied at a rate sufficient to maintain a dissolved oxygen level in said mixture effective to supply the biological oxygen demand of the digesting material before the temperature of said mixture reaches 55° C. and at a rate sufficient to maintain the dissolved oxygen level in said mixture above about 1.0 mg/l. after the temperature of said mixture reaches 55° C.

* * * * *

UNITED STATES PATENT AND TRADEMARK OFFICE
CERTIFICATE OF CORRECTION

PATENT NO. : 4,292,328
DATED : September 29, 1981
INVENTOR(S) : Coulthard et al.

It is certified that error appears in the above-identified patent and that said Letters Patent are hereby corrected as shown below:

Claim 1, Column 25, Line 8;   insert "of" after "essentially"

Signed and Sealed this

Thirtieth Day of March 1982

[SEAL]

Attest:

GERALD J. MOSSINGHOFF

Attesting Officer   Commissioner of Patents and Trademarks